US005516925A

United States Patent [19]
Pedersen et al.

[11] Patent Number: 5,516,925
[45] Date of Patent: May 14, 1996

[54] AMINO ACID CHELATES HAVING IMPROVED PALATABILITY

[75] Inventors: Mark Pedersen, Kaysville; H. DeWayne Ashmead, Fruit Heights, both of Utah

[73] Assignee: Albion International, Inc., Clearfield, Utah

[21] Appl. No.: 294,632

[22] Filed: Aug. 23, 1994

[51] Int. Cl.⁶ .......................... C07F 13/00; C07F 11/00; C07F 15/00
[52] U.S. Cl. .............................. 556/50; 556/63; 556/116; 556/134; 556/148
[58] Field of Search .......................... 556/50, 63, 116, 556/134, 148

[56] References Cited

U.S. PATENT DOCUMENTS

| | | | |
|---|---|---|---|
| 4,216,143 | 8/1980 | Ashmead | 260/113 |
| 4,216,144 | 8/1980 | Ashmead | 260/115 |
| 4,599,152 | 7/1986 | Ashmead | 204/72 |

*Primary Examiner*—Porfirio Nazario-Gonzales
*Attorney, Agent, or Firm*—Thorpe, North & Western

[57] ABSTRACT

A palatable metal amino acid chelate for administration to humans and other warm-blooded animals is disclosed wherein there are sufficient ligands to provide ionic and coordinate covalent bonds equal to the coordination number of the central metal ion while, at the same time, maintaining charge balance in the chelate molecule. There must be at least one ligand of the polydentate type which must be an α-amino acid with the further proviso that any unidentate or polydentate ligand(s) must be charge balanced organic ligands. Charge balancing may be accomplished by means of an organic acid and dicarboxylic, hydroxycarboxylic, hydroxydicarboxylic or hydroxytricarboxylic acids in particular, which maintains the chelate molecule as an optimum pH for purposes of stability and palatability.

23 Claims, No Drawings

AMINO ACID CHELATES HAVING IMPROVED PALATABILITY

BACKGROUND OF THE INVENTION

This invention relates to amino acid chelated mineral compositions containing amino acid ligands which have improved palatability. More particularly, this invention relates to amino acid chelated mineral compositions wherein the coordination number of the metal is satisfied by an organic electron donor moiety and wherein the ligands are charge balanced to neutralize electron donor or Lewis Base sites resulting in amino acid chelates which are essentially free of objectional taste.

In the formation of metal complexes and/or chelates there are actually two valencies or binding sites for the central metal ion which should be considered. The first is the "primary valence" (oxidation state) exhibited by the metal ion, e.g. copper as copper(I) or cuprous (+1) and copper(II) or cupric (+2) ions; iron as iron(II) or ferrous (+2) and iron(III) or ferric (+3) ions, zinc as zinc(II) or zinc (+2) ions; calcium as calcium(II) or calcium (+2) ions; manganese as manganese(II) or manganese (+2) and manganese(III) or manganese (+3) ions; magnesium as magnesium(II) or magnesium (+2) ions; chromium as chromium(II) or chromium (+2) and chromium(III) or chromium (+3) ions and cobalt as cobalt(II) or cobalt (+2) and cobalt(III) or cobalt (+3) ions. Additonally, there is a secondary valency of a central metal ion directed to specific position in the coordination sphere which is the total number of bonds the metal forms with ligands, i.e. a molecule containing a functional grouping which can serve as an electron donor and form a coordinating bond. Ligands can vary from molecules as simple as water or ammonia to complex polydentate ligands having two or more electron donor sites capable of chelate formation.

The secondary valence of the central metal ion is referred to as the "coordination number". Numbers ranging from 2 to 12 have been observed but numbers of 2, 4 and 6, and sometimes 8, are the most common. Of the metals of interest in the present invention, coordination numbers of 2 and 4 are found mostly in Cu(I) with 2 being the most common. Copper(II) has coordination numbers of 4 or 6. Iron(II) has a coordination number of 6 and Iron(III) has coordination numbers of 4 or 6. Zinc(II) has coordination numbers of 4 or 6. Calcium has coordination numbers of 6 and 8. Magnesium(II), manganese(II) and manganese(III) each have a coordination number of 6. Additionally, cobalt(II), cobalt(III), chromium(II) and chromium(III) each have a coordination number of 6.

The coordination number assigned to a central metal ion depends on a number of variables or factors. Representative of these are the ratio of the radius of the central metal ion to that of the attached ligands. As the ligand gets larger fewer ligands can coordinate with the metal. Also, ligands that transfer a negative charge to the metal also result in reduced coordination numbers.

When a metal combines with an electron donor ligand, a complex or coordination compound is formed. When the electron donor contains two or more donor groups tied together in some way, the ligand is referred to as a polydentate ligand, e.g. a bidentate ligand has two donor groups, and the resulting complex is a chelate. The essential and characteristic feature found in all chelates is formation of a ring of bonded atoms between the ligand and the metal atom. For ring formation to occur, the electron donor molecule must contain two or more groups that can each combine with the metal atom. Groups or atoms (e.g. oxygen, nitrogen, hydroxyl, and amino) must be present that can coordinate with the metal atom through their electron pairs. These donor groups must be separated from each other by chains of suitable length to form sterically permissible rings.

α-Amino acids comprise a group of ligands that have been used to chelate minerals. It is known that α-amino acid chelates form a stable product having one or more five-member rings formed by reactions between the carboxyl oxygen and the α-amino group of an α-amino acid with the metal ion. Such a five-member ring is defined by the metal atom, the carboxyl oxygen, the carbonyl carbon, the a-carbon, and the α-amino nitrogen and is generally represented by the Formula I. However, the actual structure will depend upon the ligand to metal mole ratio and whether monosubstituting unidentate ligands are also utilized. The ligand to metal ratio is at least 1:1 and is preferably 2:1, but in certain instances may be 3:1 or even 4:1 with bidentate ligands, depending upon the coordination numbers of the metal ion and the size and steric configuration of the ligands. If monodentate ligands are used in conjunction with a single bidentate ligand, such as an α-amino acid, then ratios could be up to 7:1 for calcium with a coordination number of eight. Most typically, an amino acid chelate may be represented at a ligand to metal ratio of 2:1 according to the following formula:

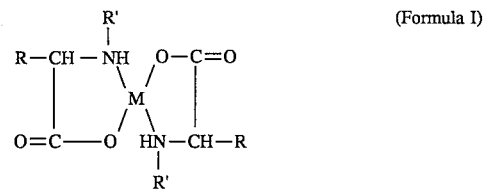

(Formula I)

In the above formula M is a member selected from the group consisting of copper, iron, manganese, zinc, magnesium, calcium, cobalt and chromium. The R moieties can be the same or different, i.e. can represent dissimilar amino acid ligands making up the chelate. When R is H, the amino acid is glycine, the simplest of the α-amino acids. However, R could represent any of the side chains of the other twenty or so naturally occurring α-amino acids derived from proteins or additionally additional metabolic α-amino acids any synthetically produced α-amino acid. R' is a member selected from the group consisting of H or [—C(O-)CHRNH$_2$—]$_e$H wherein R is as defined above and e is an integer of 1 or 2. When e is 1 or 2 the ligand becomes a di- or tripeptide of amino acids (i.e. hydrolyzed protein fragments) or any synthetically produced α-amino acid or amino acid chains. These α-amino acids all have the same configuration for the positioning of the carboxyl oxygen and the α-amino nitrogen. In other words, the chelate ring is defined by the same atoms in each instance. The American Association of Feed Control Officials (AAFCO) has also issued a definition for an amino acid chelate. It is officially defined as the product resulting from the reaction of a metal ion from a soluble metal salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the metal forming the chelate, i.e. iron amino acid chelate, copper amino acid chelate, etc.

According to the above, amino acid chelates can also be formed using dipeptide or tripeptide ligands. A representative tripeptide is shown in Formula II:

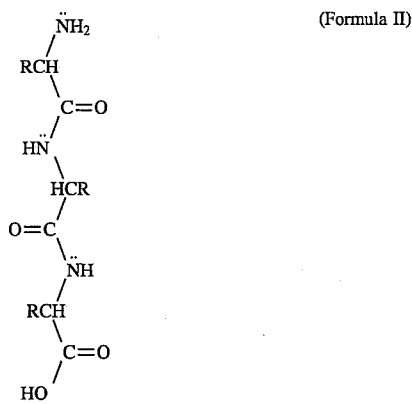

(Formula II)

where R is as defined above. The R groups are independent of each other and can represent a tripeptide of the same or different amino acids. Ligands larger than tripeptides possess at least two drawbacks. First, sterically, they may be too large in size to conveniently form a chelate wherein all of the coordination sites are occupied by an electron donor. Secondly, they would have a molecular weight which would be too great for direct intestinal absorption of the chelate formed. Generally, peptide ligands will be derived by the hydrolysis of protein. However, peptides prepared by conventional synthetic techniques or genetic engineering can also be used. When a ligand is a di- or tripeptide, R, as defined in Formula I, can be H, or the side chain of any other naturally occurring or synthetically prepared amino acid and e can be an integer of 1 or 2. When e is 1 the ligand will be a dipeptide and when e is 2 the ligand will be a tripeptide, but the moieties of chelation will derive from the carboxyl end of the dipeptide or tripeptide chain, rather than the amino terminis. The carboxyl oxygen and nearby a-nitrogen of the same terminal amino acide will be the chelating portions of the dipeptide or tripeptide chain. As noted above, the R moieties are independent in that different R groups can be contained on ligands forming the chelate and, in the case of di- or tripeptides, different amino acids can make up the peptide chain.

The structure, chemistry, and bioavailability of amino acid chelates is well documented in the literature, e.g. Ashmead et al., *Chelated Mineral Nutrition in Plants, Animals and Man,* (1982), Chas. C. Thomas Publishers, Springfield, Ill.; Ashmead et al., *Intestinal Absorption of Metal Ions and Chelates,* (1985), Chas. C. Thomas Publishers, Springfield, Ill.; Ashmead et al., *Foliar Feeding of Plants with Amino Acid Chelates,* (1986), Noyes Publications, Park Ridge, N.J.; *The Roles of Amino Acid Chelates in Animal Nutrition,* (1993), Noyes Publications, Park Ridge, N.J.; as well as in U.S. Pat. Nos. 4,020,158; 4,167,564; 4,216,143; 4,216,144; 4,599,152; 4,774,089; 4,830,716; 4,863,898 and others. Flavored effervescent mixtures of vitamins and amino acid chelates for administration to humans in the form of a beverage are disclosed in U.S. Pat. No. 4,725,427.

In the field of mineral nutrition, amino acid chelates have increasingly been recognized as providing certain advantages over inorganic mineral salts. One advantage is attributed to the fact that these chelates are readily absorbed in the gut and mucosal cells by means of active transport as though they were amino acids or small peptides. In other words, the minerals are absorbed along with the amino acids as a single unit utilizing the amino acids as carrier molecules. Since this method of absorption does not involve the absorption sites for free metal ions, the problems of competition of ions for active sites and suppression of one nutritive mineral element by another are avoided. Other advantages of amino acid chelates include stimulation of gonadotropic hormones, U.S. Pat. No. 4,774,089; delivery of metal ions to targeted tissue sites, U.S. Pat. No. 4,863,898; and enhancement of the immune system, U.S. Pat. No. 5,162,369.

Despite these advantages, use of amino acid chelates for human and animal consumption has the drawback of a metallic flavor or aftertaste that some people and animals find unpleasant or disagreeable. Thus, amino acid chelates have had to be taken in capsules and other forms that avoid this aftertaste. Use of amino acid chelates in nutritional beverages has also been limited by this disagreeable flavor. It was commonly believed that the metallic aftertaste of mineral amino acid chelates was due to the metal portion of the chelates. However, it has now been found that the aftertaste of the chelates may be due to a variety of factors associated with incomplete filling of all coordination binding sites of the metal ion and the charge associated with the ligand following the chelation of the ligand(s) to the metal ion.

In view of the foregoing, it will be appreciated that amino acid chelates having improved palatability would be a significant advancement in the art.

OBJECTS AND SUMMARY OF THE INVENTION

It is an object of the invention to provide a chelated mineral composition that eliminates the problem of a metallic aftertaste or flavor while retaining the advantages of amino acid ligands and the bioavailability of the metal ion.

It is also object of the invention to provide amino acid chelated minerals that are essentially taste-free or lack a disagreeable flavor or aftertaste so that they can be taken in tablets, beverages, powders, and the like.

It is another object of the invention to provide a method of making amino acid chelated minerals that are essentially taste-free or lack a disagreeable flavor or aftertaste.

It is a further object of the invention to provide amino acid chelated mineral compositions in which the coordination sites of the metal ion are bound with donor electron ligands of the polydentate type or combinations of polydentate and unidentate type and where there are charge neutralizations of free amino, hydroxyl, or other electron donor groups of amino acid ligands.

These and other objects are achieved by providing an amino acid chelate wherein there are sufficient ligands to provide ionic, covalent and coordinate covalent bonds equal to the coordination number of the central metal ion while, at the same time, maintaining charge balance in the chelate molecule. There must be at least one ligand of the polydentate type which must be an α-amino acid with the further proviso that any unidentate or polydentate ligand(s) must be charge balanced organic ligands.

DETAILED DESCRIPTION OF THE INVENTION

Before the present taste-free amino acid chelates and method of making them are disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the content clearly dictates otherwise.

In describing and claiming the present invention, the following terminology will be used in accordance with the definitions set out below.

As used herein, "taste-free", "palatable" or "improved palatability" means that the amino acid chelates of the present invention are substantially lacking the metallic aftertaste or disagreeable flavor of prior art amino acid chelates to the extent that they have a more pleasant taste to the consuming warm-blooded host, i.e. an animal or human being. This is not to say that taste-free amino acid chelates are completely lacking a flavor or taste.

As stated above, it had been thought that the metal moieties of amino acid chelates were responsible for the metallic aftertaste associated therewith. However, it has now been discovered that there are various parameters or factors associated with the less pleasant taste of such metal amino acid chelates. One parameter is that the coordination number of the metal in the chelate must be satisfied by an electron donor group of an organic ligand which forms an ionic or coordinate bond which is sufficiently stable within a pH range that the bond will not be broken or the ligand dissociate from the metal within that pH environment. This range varies with each metal ion as illustrated in following Table I. Water ($H_2O$) is not sufficiently stable as a ligand to satisfy this requirement. At least one ligand must be of the polydentate type of the α-amino acid configuration. Preferably two or more ligands will be of the polydentate type and are preferably α-amino acid ligands. A second factor or parameter is that the charge attributed to donor electrons not associated with binding to the metal ion must be balanced. In other words, any Lewis Base or electron donor sites such as found in amino, hydroxy, alkoxy, anionic or similar groupings must be neutralized or balanced by appropriate means or functionalities. Such taste-free amino acid chelates may be represented by Formula III:

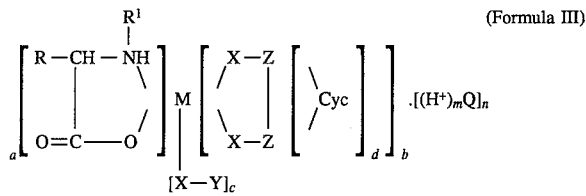

(Formula III)

where a is a number of 1 to 3, b is a number of 0 to 2, c is a number of from 0 to 6, d is a number of 0 or 1, n is a number ranging from 0 to 10 and m is a number of 1 to 3. While 0 (zero) is technically not a number, in the sense that a number means a positive value, its use in the present invention is definite in meaning that, when the number is 0, the group within the brackets represented by that number is not present in the formula. Moreover, any number can represent a partial or fractional amount. M is a member selected from the group consisting of Cu(I), Cu(II), Fe(II), Fe(III), Mn(II), Mn(III), Zn(II), Mg(II), Ca(II), Co(II), Co(III), Cr(II) and Cr(III). R is H or a side chain of any naturally occurring or synthetic α-amino acid. $R^1$ is a member selected from the group consisting of H, $R^3$, $R^{41}C(O)$, $R^5SO_2$ and $[—C(O)CHRNH_2—]_eH$ wherein R is as defined above $R^3$ is alkyl, $R^4$ is alkyl or the residue of a polycarboxylic acid, $R^5$ is alkyl or aryl and e is an integer of 1 or 2. X is independently a member selected from the group consisting of O, $OR^2$, S, $SR^2$, $NH_2$ and $NHR^2$, When d is 0, Z is independently a member selected from the group consisting of CH, $CH_2$, CHR and C=O. When d is 1, Z is CH and Z, Z and Cyc combine to form an additional ring which may be substituted or unsubstituted and may be cyclic or aromatic. $R^2$ is a member selected from the group consisting of H and alkyl. The term alkyl represents any $C_1$ to $C_{10}$ alkyl group and may be straight or branched chained. Aryl represents any aromatic ring which is functional but is preferably phenyl. Alkyl and aryl groups can also be substituted by moieties which do not detract from the functionality of the invention. For example, functional substituents comprising amines, esters, OH, carboxylic acids and the like can be present provided the overall ligand is charge balanced and otherwise palatable. Y represents any unidentate organic ligand or polydentate organic ligand coordination bonded to the metal at a single electron donor site. $[(H^+)_mQ]_n$ represents any organic acid, and preferably a member selected from the group consisting of dicarboxylic, hydroxycarboxylic, hydroxydicarboxylic and hydroxytricarboxylic acids. Most preferable are those acids selected from the group consisting of citric, malic, tartaric, oxalic, malonic, succinic, maleic, fumaric and lactic acids.

Under the above formulae, "—X—Z—Z—X—" can be representative of an α-amino acid, a dicarboxylic acid such as citric, malic, tartaric, oxalic, malonic, succinic, maleic and tartaric acids listed above, an alkylene diamine, or any other number of bidentate ligands which have been utilized in chelate formations. When —X—Z—(Cyc)—Z—X— is such that —Z—(Cyc)—Z— combine to form an aromatic ring, ligands such as vanillin or any of those disclosed in copending application Ser. No. 08/293,516, filed Aug. 19, 1994 may be used. Also, "$[(H^+)_mQ]_n$" is symbolic of any variety of organic acids, carboxylic or sulfonic, of which acetic, propionic, butyric, benzene sulfonic, and the dicarboxylic, hydroxycarboxylic, hydroxydicarboxylic and hydroxytricarboxylic acids listed above are representative. The dicarboxylic, hydroxycarboxylic, hydroxydicarboxylic and hydroxytricarboxylic acids are particularly preferred.

In defining the above it is to be noted that no claim is made as to the novelty of any particular ligand or even any combination of ligands in this invention. Therefore, each of the substituents making up the ligand or combination of ligands making up the chelate molecule is not thought to require specific definition because there are numerous amino acid chelated molecules readily discernable to one skilled in the art which are within the scope of the present invention. Rather, the invention resides in the discovery that the coordination sites of a central metal ion must be satisfied by coordination or ionic bonding of an organic ligand, at least one of which must be an α-amino acid, coupled with charge balance of the entire molecule to provide an α-amino acid chelate of sufficient stability that the moieties which contribute to the aftertaste of such a molecule are neutralized or balanced.

This may be accomplished in a number of ways. In one embodiment, conjugating the free amine groups of an amino acid following chelate formation with an organic moiety such as an alkyl halide, an aldehyde, ketone, an acid chloride of a carboxylic acid or sulfonic acid results in a derivatized amino acid chelate that substantially lacks the disagreeable flavor or metallic aftertaste of amino acid chelates of Formula I.

In a second embodiment, certain amino acids are, in and of themselves, charged balanced when all of their donor electron sites are involved in coordination and/or ionic bonding with all of the coordination bonding sites of the central metal ion.

In yet another embodiment, ligands having an aromatic ring such as disclosed and claimed in U.S. Pat. No. 5,292,729 and 1,2-disubstituted aromatic ligands such as disclosed and claimed in copending application Ser. No. 08/293,516, filed Aug. 19, 1994 may be charged balanced through selection and optimization of the amino acid and aromatic or cyclic ligands.

In a further embodiment, the addition of an organic acid to an amino acid chelate having electron donor properties or which is sufficiently "electron rich" may result in a composition wherein the acid contributes to the strengthening of the coordination and or ionic bonds at the coordination sites of the central metal ion and also balances any extra electron activity in the ligands forming the chelate. Whether the action of the acids is by means of hydrogen bonding, ionic bonding, or simply pH balancing in not known. Also, carboxylic acid anions may serve as electron donors and form coordinate bonds with the central metal cation. Therefore, the carboxylic acids may serve as unidentate, bidentate or tridentate ligands. Whatever the means of action, it has been found that through the use of appropriate amounts of acids, an otherwise less palatable amino acid chelate is rendered tastefree or taste acceptable to a consuming host. Of the acids which may be utilized, it has been found preferable to employ fruit acids or other acids which are primarily dicarboxylic acids, hydroxycarboxylic, hydroxydicarboxylic or hydroxytricarboxylic acids such as acids selected from the group consisting of citric, malic, tartaric, oxalic, malonic, succinic, maleic, fumaric and lactic acids. This listing is considered to be representative and not all inclusive. In balancing the charge and/or maintaining the proper pH range, these acid ligands may be present in fractional molar amounts. Hence the number "n" may be any amount ranging from 0 up to about 10. When "n" represents a positive number or value the acid will represent a number of between about 0.1 and 10. Preferably, the acid will be present in amounts such that n is a number of between about 0.5 and 5. The upper limit may be determined empirically based on the ligand makeup of the chelate in order to maintain charge balance.

Compositions according to Formula III wherein $R^1$ is a member selected from the group consisting of H $R^3$, $R^4C(O)$ and $R^5SO_2$ and $R^2$ is a member selected from the group consisting of H and alkyl, can be made from amino acid chelates according to Formula I by ammonolysis of halides, reductive amination of aldehydes and ketones, and reaction with acid chlorides of carboxylic acids or sulfonic acids. In each of these types of reactions, the amine nitrogen of a five-membered ring unites with a reactive group to form a composition according to Formula III. In each of the following reactions, R represents H or other side chain of any naturally occurring or synthetic α-amino acid or di- or tripeptide thereof, and M is a metal ion selected from the group consisting of Fe, Cu, Mg, Zn, Ca, Mn, Cr and Co. The reaction of an alkyl halide with an amino acid chelate is represented by the following reaction scheme:

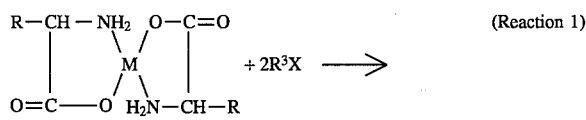 (Reaction 1)

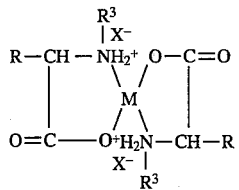

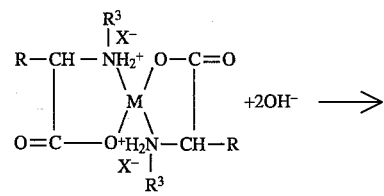

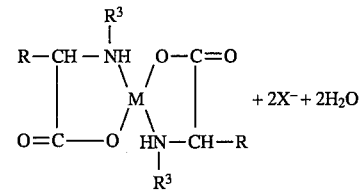

where $R^3$ is alkyl or substituted alkyl.

The reaction of an aldehyde with an amino acid chelate according to Formula I is represented by the following reaction scheme:

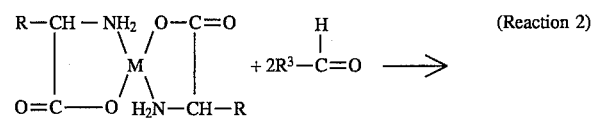 (Reaction 2)

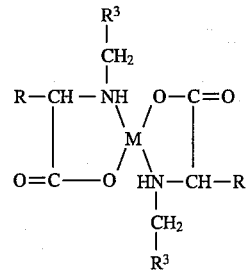

where $R^3$ is alkyl or substituted alkyl.

The reaction of a ketone with an amino acid chelate according to Formula I is represented by the following reaction scheme:

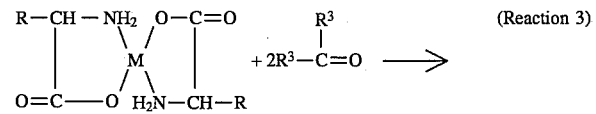 (Reaction 3)

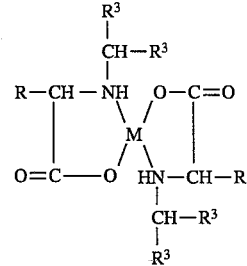

where $R^3$ are independently alkyl or substituted alkyl.

The reaction of an acid chloride of a carboxylic acid with an amino acid chelate according to Formula I is represented by the following reaction scheme:

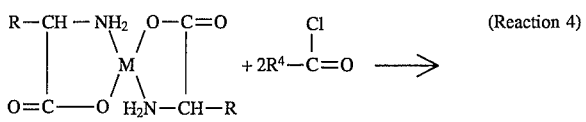

(Reaction 4)

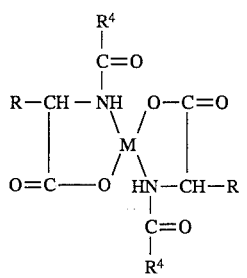

where $R^4$ is alkyl, substituted alkyl including the residue of any appropriate organic acid and particularly a polycarboxylic acid such as citric acid.

The reaction of an acid chloride of a sulfonic acid with an amino acid chelate according to Formula I is represented by the following reaction scheme:

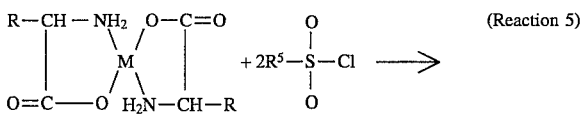

(Reaction 5)

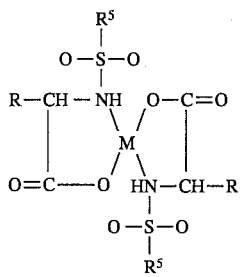

where $R^5$ is alkyl, aryl or substituted alkyl or aryl.

The following examples illustrate numerous taste-free amino acid chelates falling within the scope of the present invention and means of their preparation. The data presented show the best mode presently known of practicing the invention.

EXAMPLE 1

Asparigine is a tridentate ligand having one ionic acid ligand and two neutral amine coordinating ligands. Zinc cations have a +2 charge and a coordination number of 6. Two moles of sodium asparigine are added to one mole of zinc(II) chloride in water. It was found that all three electron donor sites of the asparigine tridentate ligand combined with the six $Zn^{++}$ coordination sites resulting in a precipitate comprising a zinc asparigine chelate which, after washing, is free of the astringent, metallic taste of zinc.

EXAMPLE 2

Glycine is a bidentate ligand having one ionic acid ligand and one neutral amine coordinating ligand. Three moles of glycine are added to a water solution of one mole of $FeCl_3 \cdot 6H_2O$. To the resulting solution was added three moles of NaOH. A precipitate was collected and washed with water. The precipitate was found to be ferric tris glycinate. Fe(III) has a coordination number of 4 or 6. In the present situation it was found that the two electron donor sites on each of the three moles of glycine had coordinated with the Fe(III) ion resulting is an iron tris glycinate which was free of the usual metallic taste.

EXAMPLE 3

Glycine is a bidentate ligand with one acidic ligand and one neutral amine coordinating ligand. Citric acid is a tridentate ligand having three acidic sites. Due to its steric configuration citric acid may not allow all three sites to form coordination bonds with a single metal ion. Additionally, citric acid is useful in maintaining optimum pH in balancing charge in the chelate molecule. Calcium cations have a +2 charge and a coordination number of six or eight. Calcium ions are relatively small and the strength of the coordinate bonds vary with the pH. Above a pH of about 9 or 10 the coordinate bond is weak, below a pH of about 6 the bond is also weak. Therefore, a formulation which balances the electron charge and maintains the pH within an optimum range provides both a palatable and stable chelate system. One mole of calcium bis glycinate (188 gm) is added one mole of citric acid (192 gm) in two liters of water. The resulting product is stable at a pH of between about 6 and 10 and is free of the objectionable taste of calcium bis glycinate.

EXAMPLE 4

Cupric cations have a +2 charge and a coordination number of 4 or 6. Glycine is a bidentate ligand having one acid and one neutral amine binding site. Niacinamide provides two neutral ligands which forms chelate bonds that are most stable in a pH range of 8–11. One mole of a soluble copper salt is reacted with two moles of glycine, one mole of niacinamide and 0.5 mole of citric acid. When purified, a stable copper amino acid chelate is formed which is essentially taste free.

EXAMPLE 5

Zinc cations have a +2 charge and a coordination number of 4 or 6. Alanine is a bidentate ligand having one acid and one neutral amine binding site. Vanillin is a ligand providing two binding sites at adjacent hydroxy and methoxy groups on an aromatic ring. One mole of zinc chloride is reacted with two moles of alanine and one mole of potassium vanillate. A stable yellow zinc amino acid vanillate chelate is formed which is essentially taste free.

EXAMPLE 6

A calcium bis lysinate stabilized with tartaric acid is prepared by adding one half mole of tartaric acid to one mole of calcium bis lysinate in water. The resulting product is dried. The product formed is a calcium bis lysinate/tartrate chelate which is essentially taste free and stable at a pH range of between about 5 to 10.

EXAMPLE 7

A chromium(III) bis glycinyl monoaspartate stabilized with citric acid is prepared by reacting one mole of a soluble chromium(III) salt with two moles of sodium glycinate and one mole of monosodium aspartic acid in water and removing the saline brine. One half mole of citric acid is then added and the resulting product is dried. The product formed is a chromium bis glycinyl monoaspartate/citrate chelate which is essentially taste free and stable at a pH range of between about 6 to 14.

EXAMPLE 8

An iron(III) lysyl glycerophosphate stabilized with malic acid is prepared by reacting one mole of ferric sulfate, one mole of lysine and one mole of calcium glycerophosphate in water. A precipitate of calcium sulfate is formed and the filtrate is separated. To the filtrate is added one mole of malic acid. The product formed is dried and is an iron(III) lysyl glycerophosphate/malate which is essentially taste free and stable at a pH range of between about 4 and 11.

EXAMPLE 9

A calcium glutamyl ureate stabilized with fumaric acid is formed by reacting one mole of a soluble calcium salt, one mole of disodium glutamate and one mole of urea in water. The brine is removed and to this chelate is added one half mole of fumaric acid. The resulting product is dried and is a calcium glutamyl ureate/fumarate which is essentially taste free and stable at a pH range of about 6 to 9.

EXAMPLE 10

A calcium asparaginyl lactate is formed by combining one mole of a soluble calcium salt, one mole of monosodium asparagine and one mole of lactic acid in water. The brine is removed and the resulting product is dried and is essentially taste free and stable at a pH range of between about 7 and 10.

EXAMPLE 11

A copper(II) bis glycinate according to Formula I is prepared and reacted according to Reaction 1 with stoichiometric amounts of methyl chloride and sodium hydroxide forming a substituted copper(II) bis glycinate according to Formula III where R is H and $R^3$ is methyl, a is 2, b, c and n are 0.

EXAMPLE 12

A copper(II) bis glycinate according to Formula I is prepared and reacted according to Reaction 2 with stoichiometric amounts of acetaldehyde forming a substituted copper(II) bis glycinate according to Formula III where R is H, $R^3$ is methyl, a is 2 and b, c and n are 0.

EXAMPLE 13

A copper(II) bis glycinate according to Formula I is prepared and reacted according to Reaction 3 with stoichiometric amounts of acetone forming a substituted copper(II) bis glycinate according to Formula III where R is H and $R^3$ is methyl, a is 2, b, c and n are 0.

EXAMPLE 14

A copper(II) bis glycinate according to Formula I is prepared and reacted according to Reaction 4 with stoichiometric amounts of acetyl chloride forming a substituted copper(II) bis glycinate according to Formula III where R is H and $R^4$ is methyl, a is 2, b, c and n are 0.

EXAMPLE 15

A copper(II) bis glycinate according to Formula I is prepared and reacted according to Reaction 5 with stoichiometric amounts of benzene sulfonylchloride forming a substituted copper(II) bis glycinate according to Formula III where R is H and $R^5$ is phenyl, a is 2, b, c and n are 0.

EXAMPLE 16

When formulating amino acid chelates such that the coordination sites of the central metal ion are satisfied by coordinate or ionic bonding with appropriate ligands, there are also optimal pH ranges in which the amino acid chelates are most stable. These ranges coincide with the balancing of the charges on the ligands and the metal. Using glycine as an example ligand which satisfies all coordination bonding sites, the pH ranges listed in Table I are preferred for each mineral specified.

| Metal Ion | Coordination Number | No. Glycine Ligands | pH Range |
|---|---|---|---|
| Cu (I) | 2,4 | 1,2 | 2–5 |
| Cu (II) | 4,6 | 2,3 | 8–12 |
| Fe (II) | 6 | 2,3 | 6–12 |
| Fe (III) | 4,6 | 3 | 1–14 |
| Mn (II) | 6 | 2,3 | 7–13 |
| Mn (III) | 6 | 2,3 | 8–12 |
| Zn (II) | 4,6 | 2,3 | 6–12 |
| Mg (II) | 6 | 2,3 | 6–12 |
| Ca (II) | 6,8 | 2,3,4 | 6–12 |
| Co (II) | 6 | 2,3 | 8–13 |
| Co (III) | 6 | 2,3 | 3–8 |
| Cr (II) | 6 | 2,3 | 6–12 |
| Cr (III) | 6 | 2,3 | 6–12 |

In each of the above, the number of ligands may be partially satisfied by other polydentate of unidentate ligands. For example citric acid could replace one or more glycine ligands provided a glycine ligand was part of the chelate. Also, even though the coordination number of the metal ion is satisfied, citric acid or any other appropriate acid could be used to both balance the charge on the ligand as well as to provide the optimal pH range to the chelate for purposes of stability. In each instance, the palatability of the chelate will be much improved over that where there is no satisfaction of the coordination binding sites or charge balancing of the ligands.

The utility of the chelates having improved palatability is the same as that which is already well documented in the prior art for administration to warm-blooded animals to improve the bioavailability of the mineral and/or direct the mineral to specific target tissue sites by selecting the appropriate combination of ligands and minerals. The invention is therefore drawn to palatable amino acid chelates for administration to both human beings and animals.

We claim:

1. A mineral amino acid chelated composition wherein the coordination number of the central mineral ion is satisfied by organic ligands at least one of which is an α-amino acid polydentate ligand, and wherein the ligands are charge balanced to neutralize electron donor or Lewis Base sites, said chelated composition having the formula:

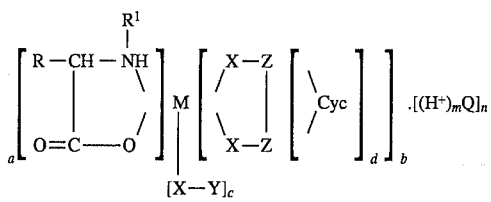

where a is an integer of 1 to 3, b is an integer of 0 to 2, c is an integer of from 0 to 6, d is an integer of 0 or 1, n is an integer ranging from 0.1 to 10 and m is an integer of 1 to 3; M is a member selected from the group consisting of Cu(I), Cu(II), Fe(II), Fe(III), Mn(II), Mn(III), Zn(II), Mg(II), Ca(II), Co(II), Co(III), Cr(II) and Cr(III); R is H or a side chain of any naturally occurring or synthetic α-amino acid; $R^1$ is a member selected from the group consisting of H, $R^3$, $R^4C(O)$, $R^5SO_2$ and $[-C(O)CHRNH_2-]_eH$ where R is as defined above, $R^3$ is alkyl, $R^4$ is alkyl or the residue of a polycarboxylic acid, $R^5$ is alkyl or aryl and e is an integer of 1 or 2; X is independently a member selected from the group consisting of O, $OR^2$, S, $SR^2$, $NH_2$ and $NHR^2$; with the proviso that when d is 0, Z is independently a member selected from the group consisting of CH, $CH_2$, CHR and C=O and when d is 1, Z is CH and Z, Z and Cyc combine to form a cyclic or aromatic ring which may be substituted or unsubstituted; $R^2$ is a member selected from the group consisting of H and alkyl; Y represents any unidentate organic ligand or polydentate organic ligand coordination bonded to the metal at a single electron donor site and $[(H^+)_mQ]_n$ represents an organic acid.

2. An amino acid chelated composition according to claim 1 wherein $[(H^+)_mQ]_n$ represents a carboxylic acid member selected from the group consisting of dicarboxylic, hydroxycarboxylic, hydroxydicarboxylic and hydroxytricarboxylic acids with n representing numerically the molar amounts of acid which are present per mole of amino acid chelate.

3. An amino acid chelated composition according to claim 2 wherein a is a number of 2 or 3.

4. An amino acid chelated composition according to claim 3 wherein $R^1$ is a member selected from the group consisting of H and $[-C(O)CHRNH_2-]_eH$.

5. An amino acid chelated composition according to claim 4 wherein M is Cu(II) and n is a number representing sufficient molar amounts of said carboxylic acid to maintain said composition at a pH within the range of between about 8 and 12.

6. An amino acid chelated composition according to claim 4 wherein M is Fe(II) and n is a number representing sufficient molar amounts of said carboxylic acid to maintain said composition at a pH within the range of between about 6 and 12.

7. An amino acid chelated composition according to claim 4 wherein M is Fe(III) and n is a number representing sufficient molar amounts of said carboxylic acid to maintain said composition at a pH within the range of between about 1 and 14.

8. An amino acid chelated composition according to claim 4 wherein M is Mn(II) and n is a number representing sufficient molar amounts of said carboxylic acid to maintain said composition a pH within the range of between about 7 and 13.

9. An amino acid chelated composition according to claim 4 wherein M is Mn(III) and n is a number representing sufficient molar amounts of said carboxylic acid to maintain said composition at a pH within the range of between about 8 and 12.

10. An amino acid chelated composition according to claim 4 wherein M is Zn(II) and n is a number representing sufficient molar amounts of said carboxylic acid to maintain said composition at a pH within the range of between about 6 and 12.

11. An amino acid chelated composition according to claim 4 wherein M is Mg(II) and n is a number representing sufficient molar amounts of said carboxylic acid to maintain said composition at a pH within the range of between about 6 and 12.

12. An amino acid chelated composition according to claim 5 wherein M is Ca(II) and n is a number representing sufficient molar amounts of said carboxylic acid to maintain said composition a pH within the range of between about 6 and 12.

13. An amino acid chelated composition according to claim 5 wherein M is Co(II) and n is a number representing sufficient molar amounts of said carboxylic acid to maintain said composition a pH within the range of between about 8 and 13.

14. An amino acid chelated composition according to claim 5 wherein M is Co(III) and n is a number representing sufficient molar amounts of said carboxylic acid to maintain said composition at a pH within the range of between about 3 and 8.

15. An amino acid chelated composition according to claim 5 wherein M is Cr(II) and n is a number representing sufficient molar amounts of said carboxylic acid to maintain said composition at a pH within the range of between about 6 and 12.

16. An amino acid chelated composition according to claim 5 wherein M is Cr(III) and n is a number representing sufficient molar amounts of said carboxylic acid to maintain said composition at a pH within the range of between about 6 and 12.

17. An amino acid chelated composition according to claim 4 wherein b and c are 0.

18. An amino acid chelated composition according to claim 5 wherein said carboxylic acid member is selected from the group consisting of citric, malic, tartaric, oxalic, malonic, succinic, maleic, fumaric and lactic acids.

19. An amino acid chelated composition according to claim 18 wherein $R^1$ is H.

20. A mineral amino acid chelated composition wherein the coordination number of the central mineral ion is satisfied by two or three α-amino acid polydentate ligands, and wherein the ligands are charge balanced to neutralize electron donor or Lewis Base sites, said chelated composition having the formula:

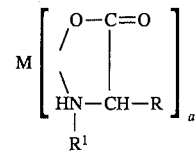

where a is an integer of 2 or 3; M is a member selected from the group consisting of Cu(I), Cu(II), Fe(II), Fe(III), Mn(II), Mn(III), Zn(II), Mg(II), Ca(II), Co(II), Co(III), Cr(II) and Cr(III); R is H or a side chain of any naturally occurring or synthetic α-amino acid; $R^1$ is a member selected from the group consisting of $R^3$, $R^4C(O)$ and $R^5SO_2$ where $R^3$ is alkyl, $R^4$ is alkyl or the residue of a polycarboxylic acid and $R^5$ is alkyl or aryl.

21. An amino acid chelated composition according to claim 20 wherein $R^1$ is $R^3$.

22. An amino acid chelated composition according to claim 20 wherein $R^1$ is $R^4C(O)$.

23. An amino acid chelated composition according to claim 20 wherein $R^1$ is $R^5SO_2$.

* * * * *